United States Patent [19]

Murray

[11] Patent Number: 5,048,542
[45] Date of Patent: Sep. 17, 1991

[54] SLEEP AID PADS

[76] Inventor: J. Kent Murray, 11999 Katy Freeway, Suite 388, Houston, Tex. 77079

[21] Appl. No.: 516,195

[22] Filed: Apr. 30, 1990

[51] Int. Cl.$^5$ ............................................. A61F 13/06
[52] U.S. Cl. ................................... 128/889; 128/892; 128/846; 128/DIG. 15
[58] Field of Search ......................... 128/380, 399–403, 128/888, 889, 892, 846, 845, 157, 117.1, DIG. 15

[56] References Cited

U.S. PATENT DOCUMENTS

| | | | |
|---|---|---|---|
| 3,670,725 | 6/1972 | Gaylord, Jr. ......................... | 128/892 |
| 3,889,684 | 6/1975 | Lebold ................................. | 128/402 |
| 4,067,330 | 1/1978 | Roache ................................ | 128/889 |
| 4,081,150 | 3/1978 | Tyson .................................. | 128/402 |
| 4,294,239 | 10/1981 | Oram et al. ................... | 128/117.1 X |
| 4,534,354 | 8/1985 | Bonner, Jr. et al. ................. | 128/402 |
| 4,572,174 | 2/1986 | Eilender et al. ..................... | 128/889 |
| 4,576,150 | 3/1986 | Auracher ..................... | 128/DIG. 15 |

Primary Examiner—Robert A. Hafer
Assistant Examiner—Kerry Owens

[57] ABSTRACT

A combination pad and strap assembly that is secured to a part of the body such as an arm, leg, or torso of a convalescing individual to prevent sleep disturbance includes a covered foam block having a first patch of fastener material on its rear side, an elastic strap having a second patch of fastener material between its ends, a tape strip fastener material that extends from one end thereon to the near vicinity of the second patch, and a tab of fastener material on the other end thereof, so that the strap can be positioned around the body part under slight tension and the tab secured to the tap strip, and then the patch on the covered foam block pressed against the patch on the strap to firmly secure the pad to the strap in any desired orientation and in a manner such that the pad will not come off as the individual tosses and turns during sleep.

7 Claims, 1 Drawing Sheet

SLEEP AID PADS

FIELD OF THE INVENTION

This invention relates generally to a support pad for use on the limbs or torso of a patient while sleeping, and particularly to a new and improved support pad or small pillow that is positively retained on the limb or torso of a patient by an elastic strap that keeps the pad in position during sleep, regardless of body movement. The pads also are useful during non-sleep periods.

BACKGROUND OF THE INVENTION

Individuals who are convalescing in nursing homes or from surgery or injury typically use one or more pillows to support an arm or a leg or other part of the body in a comfortable position, as needed. However a regular pillow can be lost as the patent tosses and turns during sleep, which causes the patient to wake up in an effort to find and reposition the pillow for better comfort. For this reason the use of a regular pillow leaves much to be desired as a support for the leg, ankle, arm or chest of a convalescing person.

An object of the present invention is to provide a new and improved support pad of the type described which will stay in position while the user sleeps.

Another object of the present invention is to provide a new and improved assembly of a support pad and an elastic strap that keeps the pad in position during sleep regardless of tossing and turning body movements.

Another object of the present invention is to provide new and improved support pads that can be affixed on opposing limbs or body parts by elastic straps to provide for separation of the limbs where necessary for maximum comfort.

SUMMARY OF THE INVENTION

These and other objects are attained in accordance with the concepts of the present invention through the provision of the combination of a resilient pad, in the nature of a small pillow, and an elastic retaining strap that removably secures the pad on a part of the patient's body. The strap has an elongated tape strip and a tab with Velcro hooked or pile fasteners particularly arranged thereon which enables the strap to be positioned around different size limbs and secured thereon under slight tension. A large patch of Velcro hook or pile faster is attached to the pad, and is engaged with an oppositely facing large patch on the strap. In this manner, the strap can be positioned and adjusted comfortably on the limb, and then the pad pressed against the strap to cause a releasable fastening to be made between the respective patches. The combination pad and strap provides sleep and bed comfort for general convalescence, and particularly for special conditions such as low back pain, pregnancy, bed confinement, post operation surgery (abdominal, back and foot), sensitive knees, and cast/skin protection, to list but a few. The pad can be positioned at any angle or direction at the discretion of the usee, or the need of the patient. The fastening of the pad to the strap in the manner disclosed herein keeps the pad firmly in position all night, regardless of body movements.

BRIEF DESCRIPTION OF THE DRAWINGS

The present invention has other objects, features and advantages that will become more clearly apparent in connection the following description of preferred embodiments, taken in conjunction with the appended drawings, in which.

DETAILED DESCRIPTION OF PREFERRED EMBODIMENTS

Figure 1:
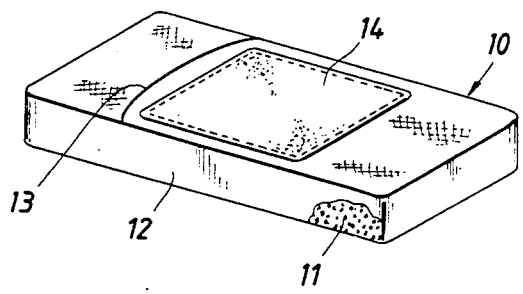
FIG. 1 is an isometric view of a pad construction in accordance with the present invention.

Referring initially to FIG. 1, a small pillow or pad 10 that preferably is made out of a generally rectangular block 11 of resilient, foamed polyethylene or the like has illustrative dimensions of approximately 4 inches in width, 8 inches in length and 2 inches in thickness. The pad 10 has a covering 12 of a moisture absorbent, ribbed cotton material including a flap 13 which overlaps an upper portion of the covering and is sewed along its outer edges thereto. The upper edge of the overlapped portion is not sewed so as to provide an opening whereby the pillow covering 12 can be removed from the resilient block 11 for cleaning. A relatively large size patch 14 of the pile element of a "Velcro" fastener is sewed to the covering 12, preferably on the same side of the covering as the flap 13. The patch 14 has dimensions of approximately 4 inches by 4 inches, and preferably is attached near the mid-portion of the block 11 as illustrated in FIG. 1.

Figure 2:
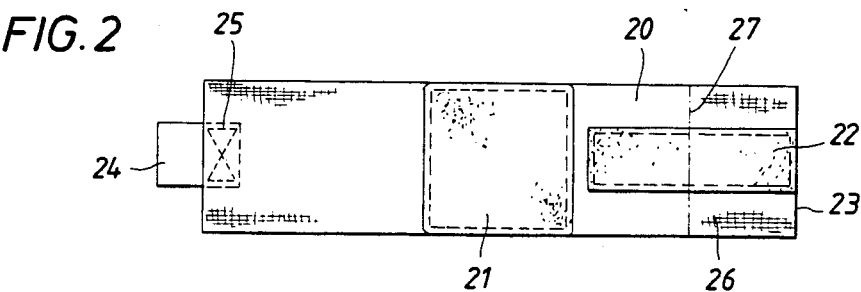
FIG. 2 is a front view of an elastic strap to which the pad on FIG. 1 is fastened.

The attachment strap 20 shown in FIG. 2 is made of a suitable elastic material having a width of about 4 inches and an unstressed length of about 15 inches. A large patch 21 having the hooked elements of a Velcro fastener is sewed to the strap 20 at a location that is approximately the middle of the length thereof. The patch 21 has dimensions to match the patch 14 on the pad 10, namely about 4 inches by 4 inches. A two inch wide tape strip 22 having Velcro pile elements is sewed along the longitudinal center line of the strap 20 and extends from the edge 23 about 6 inches toward the patch 21. A tab 24 having Velcro hook elements on its rear side is sewed centrally to the end portion 25 of the strap 20, as shown. Thus the elastic strap 20 can be positioned to encircle a limb or a cast with the back side thereof toward the inside, and then the tab 24 fastened to the tape strip 22 by pressing the tab against it. The opposite end portion 26 of the strap 20 has a transverse sew line 27 about 3 inches from the edge 23 thereof to enable excess length to be cut off without the material unraveling.

In use, the strap 20 is placed around, for example, the arm of the user under a slight but comfortable tension with the patch 21 and the tape strip 22 facing outward. The tab 24 then is pressed against the strip 22 to fasten the strap 20 around the limb. The strap 20 is adjusted so that the fastener patch 21 is facing in the appropriate direction, and then the pile element patch 14 of the pad 10 is pressed against the hooked element patch 21 on the strap 20 to releasably attach the pad to the strap. The relatively large area of hook and pile engagement provides a very positive fastening which prevents the pad from coming off the strap as the user tosses and turns during sleep. Thus the pad 10 is not lost, which would otherwise result in a sleep disturbance.

The pad 10 can have a larger size from that described above for other applications such as to leg and arm casts, for example width and length dimensions of 7 inches and 12 inches, respectively. The strap 20 that is used with a larger pad can be longer to accommodate the longer circumference of a cast. However the same width of strap material, and the same size Velcro pile and hook patch elements, are preferred. Hereagain the strap can have transverse sew lines spaced every 4 inches or so from the outer edge thereof so that excess material can be cutoff without unraveling.

Figure 3A:
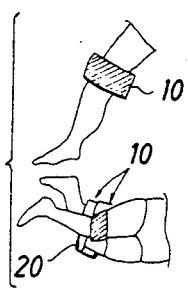
FIGS. 3A-3F are schematic views showing the locations of the pads and straps on various parts of the body.
Figure 3B:
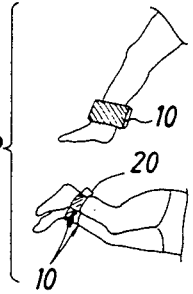
Figure 3C:
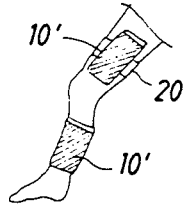
Figure 3D:
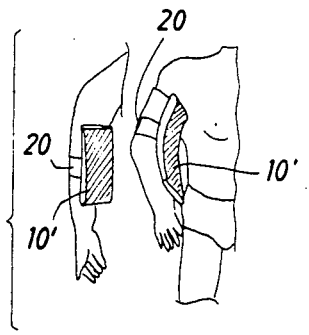
Figure 3E:
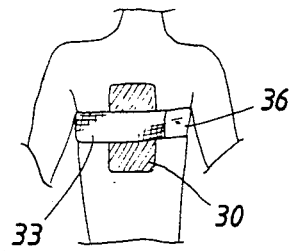
Figure 3F:
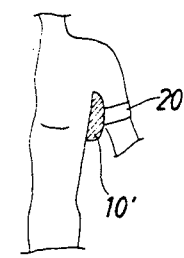

To further illustrate the uses of the present invention, FIG. 3A shows a pair of smaller pads 10 attached just above the users knees to prevent contact between sensitive skin areas during sleep. FIG. 3B shows the smaller pads attached to the inside of the ankles for providing a separation following foot surgery or the like, or for convalescing patients who have skin rubbing in the ankle bone areas which causes ulcerated sores. FIG. 3C illustrates the larger pads 101 attached inside the thigh and calf for leg cast applications. FIG. 3D shows a larger size pad 10' attached between an arm cast and the side of the body. FIG. 3E shows a pad attached to the front of the chest, which is useful following open heart surgery or lung surgery and which is described in greater detail below. FIG. 3F shows a pad 10' that is placed under the upper arm to provide comfort following breast surgery.

Figure 4:
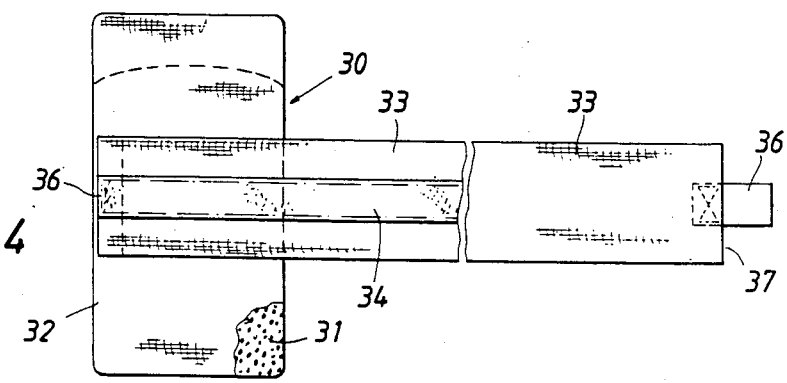
FIG. 4 illustrates another embodiment of the present invention.

Another embodiment of the present invention that is particularly adapted as a chest pillow is shown in FIG. 4. The pillow 30 is approximately the same size as the second embodiment described above, and includes a resilient block or pad 31 of foamed polyethylene covered by a case 32 made of a moisture absorbent, soft material such as ribbed cotton. As in all other embodiments of the present invention, the pad can be made out of polyester fibers or other equivalent material, and the case 32 can be made of non-woven, hydro-entangled polyester cellulose. In this instance the rear side of the case 32 can have an access flap (shown in phantom lines) so that the case can be removed from the foam block 31 for cleaning. Attached by stitching at one side edge of the case 32 and centered near the transverse centerline thereof is an elastic strap 33 that is about 4 inches wide and about 4 feet long. A tape strip 34 of the pile element of a Velcro fastener is sewed to the strap 33 along its side edges, and extends from the edge 35 where the strap 33 is attached for about 2 feet along the strap toward the free end thereof. The strap 33 crosses the mid-portion of the front of the pad 31 and then extends on outward. A rearwardly facing tab 36 that has the hooked elements of a Velcro fastener is secured to the edge 37 of the outer end of the strap 33 by sewing.

In use, the pillow 30 is positioned vertically against the chest of the patient, and then the strap 33 is wrapped around the back and to the front of the chest so that the outer end 37 having the tab 36 overlays an underlying portion of the strap. With the strap 33 under suitable tension, the tab 36 is pressed against the tape strip 34 to fasten the outer end 37 of the strap thereto. Hereagain the pillow 30 will stay firmly in place and protect the patient from experiencing more discomfort should any object or thing press inward in the region of the incision, or during coughing spells. The strap 33 helps prevent over-expansion of the chest cavity or thoracic area, which can pull out sutures or staples.

It now will be recognized that new and improved resilient pads have been disclosed that will stay on the user during sleep. Since certain changes or modifications may be made in the disclosed embodiments without departing from the inventive concepts involved, it is the aim of the appended claims to cover all such changes and modifications falling within the true spirit and scope of the present invention.

What is claimed is:

1. A strap and pad assembly for use in comforting a patient during convalescence, comprising: a resilient, generally rectangular body; a case made of a moisture absorbent material covering said body; a first patch of fastener material secured to one side of said case; a strap made of an elastic material adapted to encircle a limb of a patient, said strap having a front side and a rear side; a second patch of fastener material secured to said front side of said strap generally centrally of the length thereof; an elongated strip of fastener material secured to said front side beginning at one end thereof and extending to the vicinity of said second patch; and a rearwardly facing tab of fastener material secured to said rear side of said strap at the other end thereof, whereby said strap can be positioned around a part of the body of a user with said second patch and said strip facing outward, said tab can be pressed against said strip to fasten said tab thereto, and said case and resilient body then can be attached to said strap by pressing said first patch of fastener material against said second patch of fastener material; said first and second patches of fastener material have substantially the same width as the width of said strap.

2. The assembly of claim 1 wherein each of said first and second patches of fastener material have a length approximately equal to said width.

3. The assembly of claim 1 wherein said strap has at least one transverse sew line spaced from said one end thereof to enable excess material to be cut off without said material unraveling.

4. The assembly of claim 1 where said case has flap means for allowing said case to be removed from said body for cleaning.

5. The assembly of claim 4 wherein said first patch of fastener material is located on the same side of said case as said flap means.

6. A pad assembly adapted to be positioned on the chest of a patient and held in place by a strap that encircles the chest, comprising: a generally rectangular pillow block made of a resilient material, said block having a front side and a back side; a moisture absorbent case covering said pillow block; a strap having one end secured to a longitudinal edge of said case on the front side thereof and extending across said block to the opposite edge of said case and then outwardly of said block, said strap having an elongated strip of fastener material attached to the outer side thereof and extending from said first-mentioned longitudinal edge along said strap for a distance equal to several times the width of said pillow block; and a rearwardly facing tab of fastener material secured to the outer end of said strap, whereby said pillow block can be positioned on the chest of a user with said strap extending across the front of said pillow block, then around the chest to the back, and from the back around to the front of the chest where said tab can be pressed against said strip of fastener material to secure said pillow block firmly in position on the chest of a user.

7. A method of attaching a small pillow to the limb or other body part of a convalescing patient, comprising: providing an elastic strap having a first patch of fastener material attached to its outer side generally centrally of the ends thereof, a strip of fastener material extending from one end of said outer side to a location adjacent said first patch, and a tab of fastener material secured to the other end thereof with said fastener material on said tab facing rearward; providing a small pillow made of a rectangular block of resilient material having a front and a rear side, a moisture absorbent covering, and a second patch of fastener material attached to said covering on the rear side of said block; positioning said strap around the body part of a patient under low tension; pressing said tab against said strip to fasten said strap around said body part; positioning said pillow adjacent said strap with said first and second patches facing one another; and then pressing said patches together to secure said pillow to said strap.

* * * * *